United States Patent

Scully et al.

[11] Patent Number: 6,077,526
[45] Date of Patent: Jun. 20, 2000

[54] WOUND DRESSING

[75] Inventors: David Christopher Scully, Westend, United Kingdom; Catherine McCabe, Atlanta, Ga.

[73] Assignee: Texon UK Limited, Leicester, United Kingdom

[21] Appl. No.: 08/930,052

[22] PCT Filed: May 8, 1996

[86] PCT No.: PCT/GB96/01087

§ 371 Date: Nov. 14, 1997

§ 102(e) Date: Nov. 14, 1997

[87] PCT Pub. No.: WO96/36304

PCT Pub. Date: Nov. 21, 1996

[30] Foreign Application Priority Data

May 17, 1995 [GB] United Kingdom .................. 9509943

[51] Int. Cl.[7] .................................................. A61F 13/00
[52] U.S. Cl. .......................... 424/443; 424/445; 424/447; 424/449
[58] Field of Search ................... 424/443, 445, 424/447, 449

[56] References Cited

U.S. PATENT DOCUMENTS

| | | | |
|---|---|---|---|
| 4,655,758 | 4/1987 | Ring et al. | 604/374 |
| 5,256,477 | 10/1993 | Mahoney | 428/283 |
| 5,374,260 | 12/1994 | Lemay et al. | 604/378 |
| 5,677,028 | 10/1997 | Ravella | 428/102 |

*Primary Examiner*—Thurman K. Page
*Assistant Examiner*—Kathryne E. Shelborne

[57] ABSTRACT

A wound dressing combining a graduated density felt 1 with an absorbent fiber layer 2 in order that the aggressive absorption of the absorbent layer 2 may be regulated to acceptable rates for wound dressing usage and to ensure potentially irritative alginate absorbent fibers are isolated from the wound site. The graduated density felt 1 acts as a regulating or gate layer for the absorbent fiber layer 2 and so limits the rate that exudate from a wound can pass to the absorbent fiber layer 2. Furthermore, the regulating layer 1 effectively spreads the exudate to give a conical transmission profile enhancing wound dressing performance.

9 Claims, 1 Drawing Sheet

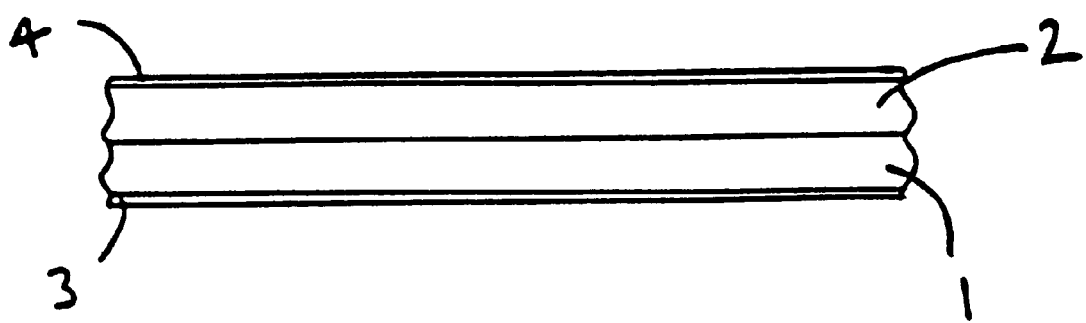

WOUND DRESSING

FIELD OF THE PRESENT INVENTION

The present invention relates to a wound dressing and more particularly but not exclusively to a wound dressing including an absorbent fibre layer,

BACKGROUND TO THE PRESENT INVENTION

It is a requirement of a wound dressing that it should protect the wound from exterior foreign body invasion etc whilst promoting healing of the wound through maintaining a desirably moist and warm environment about the wound.

Traditionally, wound dressings have comprised a non-woven web of material such as cotton wool with gauze to provide a pseudo non-adherent coating which will allow wound exudate to be absorbed whilst inhibiting incorporation of the actual wound dressing in the regenerated skin tissue of the wound.

There are readily apparent limitations with a traditional cotton wool wound dressing with regard to the amount of exudate absorption per weight of wound dressing and the bulk of this type of dressing. It will be appreciated that ideally wound dressings should be replaced as few times as possible in order to ensure the wound remains warm and moist. There is a significant temperature drop about the wound site upon each occasion that the wound dressing is removed, however, and with previous wound dressings it was necessary to replace the dressing quite frequently particularly with burns as the dressing quickly became saturated with exudate.

It is known to provide multi-component wound dressings which comprise two or more absorbent layers in order to enhance absorption capacity. One or more of the layers being replaceable when saturated. Examples of such multi-component wound dressings are given in U.S. Pat. No. 5,167,613 (The Kendall Company) and WO 93/07841 (Cummings).

Although these multi-component dressings may include hydrophobic fibres and gels, the objective is to limit wound trauma when removing the replaceable absorbent layers. Thus, the absorbent layers tend to be highly incapsulated and present several filmic barrier layers to the wound site greatly reducing the suitability of such dressings for highly exuding wounds. These multi-component dressing are most suitable for long term use in relatively slowly exuding wounds.

More recently alginate and polysaccharide fibres have been investigated for wound dressings. However, these fibres can be too aggressive with respect to the rate of exudate absorption and also may cause irritation about the wound site. Furthermore, some types of absorbent fibre may present toxicology and sterilisation problems.

OBJECTIVE OF THE PRESENT INVENTION

It is an objective of the present invention to provide a wound dressing which may incorporate aggressive absorbent fibre materials without the above mentioned problems.

SUMMARY OF THE PRESENT INVENTION

In accordance with the present invention there is provided a wound dressing comprising several layers of absorbent material secured together to form the wound dressing, the wound dressing being characterised in that at least one of the absorbent layers is a regulating layer, the regulating layer comprising a non-woven fabric selectively entangled through its depth in order to create zones of varying density and so regulate exudate flow from a wound site on one side of the regulating layer to the absorbent layer coupled to the other side and so effectively isolate in use the absorbent layer from the wound site and to regulate the absorbency rate of the absorbent layer to ensure in use the wound site remains essentially moist.

Preferably, the regulating layer and absorbent fibre layer are needled together.

Preferably, the wound dressing includes a non adherent macroporous cover for contact with the wound and a microporous backer layer.

Preferably the regulating layer is formed from a blend of polyester fibres and viscose fibres.

Preferably the edge of the wound dressing is sealed with a woven tape adhered between the top and bottom of the wound dressing or is bonded using ultrasonic welding techniques.

BRIEF DESCRIPTION OF THE DRAWINGS

An embodiment of the present invention will now be described by way of example only with reference to the accompanying drawing showing a wound dressing in cross section.

DESCRIPTION OF THE PRESENT INVENTION

Alginate or polysaccharide fibres are normally formed into a non-woven mat or web of entangled strands. These fibres are biodegradable and very absorbent typically absorbing 15 times their own weight. A typical absorbent, i.e. alginate, fibre is calcium sodium polysaccharide.

Unfortunately alginates, as indicated previously, have an aggressive moisture absorbency rate and can be irritative. Thus it is essential that no absorbent fibres or for that matter gel come into contact with the wound site.

In the present invention a graded density felt 1 is secured in association with a layer of absorbent fibre material 2. The layers 1,2 may be secured together by a range of techniques including needle entanglement to a limited depth at their interface. Needle entanglement causes entanglement between fibres in respective layers 1,2 and these tacks create a usually modest adhesion between the layers 1,2. The strength of the adhesion between the layers 1,2 is highly dependent upon the number of tacks created by the needling operation and as such the strength of adhesion can be determined to a reasonable degree by design choice. The depth of tacks is determined by the necessity to ensure none of the absorbent alginate fibres can become incident upon the wound site and so it is normal for the tacking only to penetrate at most 25% into the graded density felt layer 1.

A graded density felt is described in EP-A-0 388 062 and as will be understood from the name of this material it has a variation in density across its depth. This variation in material density is achieved by varying the degree of needle penetration and thus fibre entanglement across the material depth. Thus, a graded density felt may have a relatively loose voluminous central region and more dense surface layers. The increased density of the surface layers is achieved by more entanglement with the result that there is less fibre spacing at its surface.

This construction of a graded density felt acts as a regulator or gate within the present wound dressing. It will be understood that exudate and moisture from a wound passes into the graded density felt layer 1. The exudate passes through the layer 1 at varying rates dependent upon the density at different depths of the layer 1. It is by the nature of fluidic flow that the exudate tends to fill the volume available before progression onto higher levels of the layer 1. Thus, with a graded density felt layer 1 having both surfaces of higher density in comparison with a middle level, the exudate passes into the first surface may have its flow rate slightly retarded by the essentially filtering effect of closely entangled fibres. However, as the exudate moves into the more voluminous and less entangled central regions of the graded density felt 1 the gating or inhibition to flow is reduced and the exudate may flow into this new region more rapidly. The effect of this is to provide a cone-like spread to the exudate passage, that is to say exudate is spread over a greater area of the wound dressing upon its passage through the graded density felt 1 in comparison with the actual exuding wound site. The upper surface of the layer 1 again has a higher density and thus greater fibre entanglement and exudate flow is again to a degree inhibited although it is not prevented.

The exudate that passes through the graded density felt 1 is rapidly absorbed by the absorbent layer 2 which readily becomes a gel. However, the wound site is still kept moist by the effect of the graduated density felt layer 1. As the exudate is spread by this layer 1, even when the absorbent layer directly above the wound site becomes saturated, the exudate may still pass through and be absorbed at more inclined areas of the layer 2. The exudate within the graded density felt 1 directly below the saturated gel of layer 2 is supported and so there is little opportunity for absorbent fibres or gel of the absorbent layer 2 drifting towards the wound site.

In order to enhance wound dressing integrity it is normal to have a macroporous wound contact layer 3 and a microporous backer layer 4. These layers 3,4 help to ensure encapsulation of the wound dressing and so prevent absorbent fibres which detach themselves from the web possibly coming into contact with the wound site. The layers 3 and 4 also help to ensure the absorbent fibre layer 2 does not absorb too much moisture from the atmosphere and so make the wound dressing ineffective over a shorter period of time than is as necessary.

The wound contact layer 3 is macroporous to allow exudate to pass through to the graded density felt 1 as quickly as possible whilst providing a non or low adherent surface so that the wound dressing does not stick to the wound site and cause trauma on removal. Typically, this macroporous layer 3 is a film with perforations or slits to allow exudate passage. The film may be polyester, polypropylene or any other suitable polymer.

The microporous backer layer 4 is adhered to the absorbent fibre layer 2. However, care must be taken when a laminating technique is used as polysaccharide absorbent fibres may become "cooked" or degraded in the heating process associated with lamination. The microporous layer 4 may be perforated with small holes using hot needle techniques.

It is most convenient for the edges of the wound dressing to be sealed by an edging tape. This tape can be ultrasonically welded to the upper surfaces whether they be the outer layers 3,4 or the inner layers 1,2. The use of an edging tape ensures that no absorbent fibres or gel can migrate or drift towards the wound site about the edges of the wound dressing.

It will be understood that wound dressings can be designed for particular applications for example, a burn will exude considerable amounts of exudate whilst simple stab wounds may merely discharge blood. The use of absorbent fibres ensures that the wound dressing in accordance with the present invention can absorb relatively large amounts of exudate and thus reduce the number of times the dressing must be changed enhancing the rate of recovery.

Those skilled in the art will understand that it is possible for a burn injury to exude up to 4,000 $g/m^2$ of exudate and such levels of exudate have in the past been difficult to accommodate with previous wound dressings. The present wound dressing, provided suitable absorbent fibres are used, can easily achieve such collection rates without too rapid removal which may result in localised drying and so inhibition of wound healing rates.

As indicated previously, a suitable alginate absorbent fibre is calcium sodium polysaccharide. Typically, the alginate will constitute up to 10% by weight of the absorbent layer. An alternative fibre is known as "Oasis" and is made by Courtaulds Ltd. of Coventry England.

The graded density felt may be made of completely hydrophobic fibres such as polyester. However it has been found that a combination of hydrophobic and hydrophilic fibres has benefits in providing the graduated density felt layer 1 with a degree of absorption itself. A suitable hydrophilic fibre is a viscose. A practical composition would be between 60% and 40% polyester and 40% and 60% viscose dependent upon design parameters.

As indicated above, manufacture of graded density felt is described in EP-0-388 062 and reference should be made thereto for specific description of the necessary techniques.

Three Examples of a suitable regulator layer material are given below. In these Examples, the effects achieved by varying the weight of the final product and/or the needle penetration can be observed. As a general rule, where the weight of the final product is reduced, the absorption is reduced and handling the fabric becomes more difficult. However, when the weight of the finished product is reduced, this can be advantageous in certain applications.

It appears that as the weight of the material is increased the absorption may increase more than linearly therewith, apparently because as the weight increases there is a proportionately greater quantity of fibres in the absorbent central region.

The weight of the fibre layer(s) introduced into the loom is determined according to the desired weight of the final material. In practice the weight of said layer(s) is determined empirically, the feed of the fibres being controlled according to the actual weight of the final product.

EXAMPLE 1

A batt made up of one or more layers was produced from a fibre blend of 80% 1.7 dTex 51 mm staple viscose fibres and 20% 5.0 dTex 40 mm staple polyester fibres.

The batt was then needled in a three-stage operation In a first, tacking, stage the batt was passed between an up-stroking needle board and a down-stroking needle board, each fitted with 15×18×40×3 F222 G92919 needles marketed by Groz Beckaert. The penetration of both the top and bottom needles was 14 mm. In a next following first needling stage, the thus tacked batt (or web) was passed under a single needle board fitted with a mixture of 67% 15×18×40×3.5 R333 G1909 needles and 33% Foster 15×18× 40×3.5 CB F20 9-18-3B needles and having a needle punch density of 83 needles/$cm^2$. Needling was thus carried out using a down-stroke only; needle penetration in this stage was 6.1 mm. Thereafter in a second needling stage, the partially needled batt (or web) was passed between an up-stroking needle board and a down-stroking needle board, each fitted with a mixture of 67% 15×18×40×3.5 R333 G1909 needles and 33% Foster 15×18×40×3.5 CB F20 9-18-3B needles and having a needle punch density of 329 needles/cm$^2$ and a head speed of 509 rpm. The top penetration in this case was 4.6 mm and the bottom penetration 5.6 mm.

The final product weight was 300 g/m$^2$.

The product was satisfactory for use as a medical absorbent, with relatively dense surface regions and a less dense central region.

EXAMPLE 2

In this Example the same procedure, using the same needle boards, was followed as in Example 1 except that in the second needling stage the penetration by the needles of the down-stroking needle board was 0.2 mm and that by the up-stroking needle board 5.6 mm. Moreover in this case the needle punch density was 392 needles/cm$^2$ and the head speed 605 rpm.

The final product weight was again 300 g/m$^2$.

The products demonstrated excellent properties for use as a medical absorbent, with dense surfaces and more open centre.

EXAMPLE 3

Again in this Example the same procedure was followed as in Example 1, except that the needle punch density in the first needling stage was 86 needles/cm$^2$, and further in the second needling stage the penetration by the needles of the down-stroking needle board was 4.7 mm and that by the up-stroking needle board 5.6 mm. Moreover, in this case the needle punch density was 337 needles/cm$^2$ and the head speed 501 rpm.

The final product weight was 190 g/m$^2$.

The product was thus a material of lighter weight than the other two Examples. Such material would be particularly suitable for a use in medical applications where the absorbency required was not so high and light weight was an advantage.

The regulator layer 1 is secured to the absorbent layer 2 using a needle fibre entanglement technique. The layers 1, 2 are laid upon each other and a needle tacker board is arranged to penetrate either through the regulator layer 1 to pick up and entangle fibres from the absorbent layer 2, or vice versa. Thus, the layers 1, 2 are secured together with these fibre entanglements. The strength of the bond between layers 1, 2 is determined by the number of fibre entanglements per unit area. However, it should also be appreciated that by the nature of the needle fibre entanglement procedure the layer 1, 2 though penetrated will also be consolidated. Thus, it may be preferred to arrange for needle tacking through the absorbent layer 2 rather than regulator layer 1 where the expanded central region may be diminished. Typically, ten tacks, or pegs as they are known, per cm$^2$ is a minimum for adequate but limited location of the layers 1, 2 with respect to each other. It will also be understood that an edge tape will also contribute to securing the layers 1, 2 together.

As indicated above, one of the major detrimental effects upon wound healing rate is the number of times a dressing is removed for inspection of the wound site. It may be possible in the present wound dressing to remove merely the absorbent fibre layer 2 and any backer layer 4 in order to expose the regulator layer 1 and any exudate passing through its top surface. This exudate could be analysed to determine healing performance. A further absorbent replacement layer could then be located above the regulator layer 1 after suitable removal of any excess exudate and gel.

In order to further facilitate a removable absorbent layer whilst ensuring no absorbent fibres or gel come into contact with the wound site or skin, it may be possible to shape the regulator layer about the edge to create a resilient lip and the resultant dishing of the layer 1 would thus facilitate containment of the absorbent fibres and gel. It will be understood that polyester fibres, being heat formable, allow such structural forming. However, a proportion of specifically thermosettable fibres may be added to facilitate such structural forming.

A further possibility is that an exudate indicative layer could be added above or just below the backer layer 4 in order to show presence of exudate. This indicative layer could then be used to show when the dressing should be changed, i.e. if the indicative layer were to change colour between a dry state and an exudant contact state. Once a pre-determined area of the indicative layer had changed colour then care staff would be alerted to the necessity to change the dressing. It will be understood that natural food dyes would be most acceptable in the indicative layer in order to ensure there are no detrimental effects.

We claim:

1. A wound dressing comprising several layers 1, 2 of absorbent material secured together to form the wound dressing, the wound dressing being characterized in that at least one of the absorbent layers 1, 2 is a regulating layer 1, said regulating layer 1 comprising a non-woven fabric of material different than said absorbent layer, said regulating layer being selectively entangled through its depth to create zones of varying density thus to regulate exudate flow from a wound site on one side of the regulating layer 1 to the absorbent layer 2 coupled to the other side, said regulating layer 1 being disposed adjacent the wound site and being more dense on a side facing said wound site than on the inside of said regulating layer 1, whereby to effectively isolate in use the absorbent layer 2 from the wound site and to regulate the absorbency rate of the absorbent layer 2 to ensure in use the wound site remains moist.

2. A dressing as claimed in claim 1, wherein the regulating layer and absorbent layer are needled together to produce fibre entanglements which bond them together.

3. A dressing as claimed in claim 1 wherein the absorbent layer includes calcium sodium polysaccharide fibres.

4. A dressing as claimed in claim 1 wherein the absorbent layer includes up to 10% by weight alginate fibres.

5. A wound dressing comprising several layers 1, 2 of absorbent material secured together to form the wound dressing, the wound dressing being characterized in that at least one of the absorbent layers 1, 2 is a regulating layer 1, said regulating layer 1 comprising a non-woven fabric selectively entangled through its depth to create zones of varying density thus to regulate exudate flow from a wound site on one side of the regulating layer 1 to the absorbent layer 2 coupled to the other side, said regulating layer 1 being disposed adjacent the wound site and being more dense on a side facing said wound site than on the inside of said regulating layer 1, whereby to effectively isolate in use the absorbent layer 2 from the wound site and to regulate the absorbency rate of the absorbent layer 2 to ensure in use the wound site remains moist, said dressing being further characterized in that a substantially non-adherent macroporous wound contact layer is provided on one side of the dressing and a substantially microporous backing layer is provided on the other side.

6. A dressing as claimed in claim 5 wherein the regulating layer is removable.

7. A dressing as recited in claim 5 wherein the regulating layer is shaped about its edges to contain the absorbent layer when wet.

8. A dressing as claimed in claim 1 wherein there is provided an exudate indicative layer.

9. The wound dressing according to claim 5 wherein the absorbent layer 2 contains alginate fibres and wherein an edging tape is secured about the edge to ensure no alginate fibres become incident upon the wound site in use.

* * * * *